United States Patent [19]

Zlobinsky

[11] Patent Number: 5,003,787
[45] Date of Patent: Apr. 2, 1991

[54] CELL PRESERVATION SYSTEM

[75] Inventor: Yury Zlobinsky, Massapequa, N.Y.

[73] Assignee: Savant Instruments, Farmingdale, N.Y.

[21] Appl. No.: 466,853

[22] Filed: Jan. 18, 1990

[51] Int. Cl.$^5$ ............................................. F25D 17/02
[52] U.S. Cl. ........................................ 62/185; 62/99; 62/435; 62/434
[58] Field of Search ................ 62/201, 185, 435, 373, 62/376, 430, 434, 68, 64, 98, 99

[56] References Cited

U.S. PATENT DOCUMENTS

| | | | |
|---|---|---|---|
| 2,528,574 | 11/1950 | Booth | 62/201 |
| 3,007,319 | 11/1961 | Ogden | 62/376 |
| 4,563,883 | 1/1986 | Sitte | 62/373 |

Primary Examiner—Henry A. Bennett
Assistant Examiner—John Sollecito
Attorney, Agent, or Firm—Morrison Law Firm

[57] ABSTRACT

A cell preservation system utilizes a pre-chilled coolant stored in a coolant reservoir, which is pumped at a controlled rate into a specimen vessel containing a specimen. This allows the achievement of a controlled rate of cooling the specimen and controls the formation of crystals in the specimen. The coolant reservoir is sealed, and the coolant is pumped from the specimen vessel to the coolant reservoir, whereby heat from the pump is not entered into the specimen vessel. A magnetic stirrer is selectively controlled to maintain a uniform temperature in the specimen vessel or, alternatively, is deenergized to permit temperature stratification to occur. A heater is included in the specimen vessel for precise heat control, and for raising the temperature of the coolant in the specimen vessel to a value suitable for beginning a cooling cycle.

11 Claims, 2 Drawing Sheets

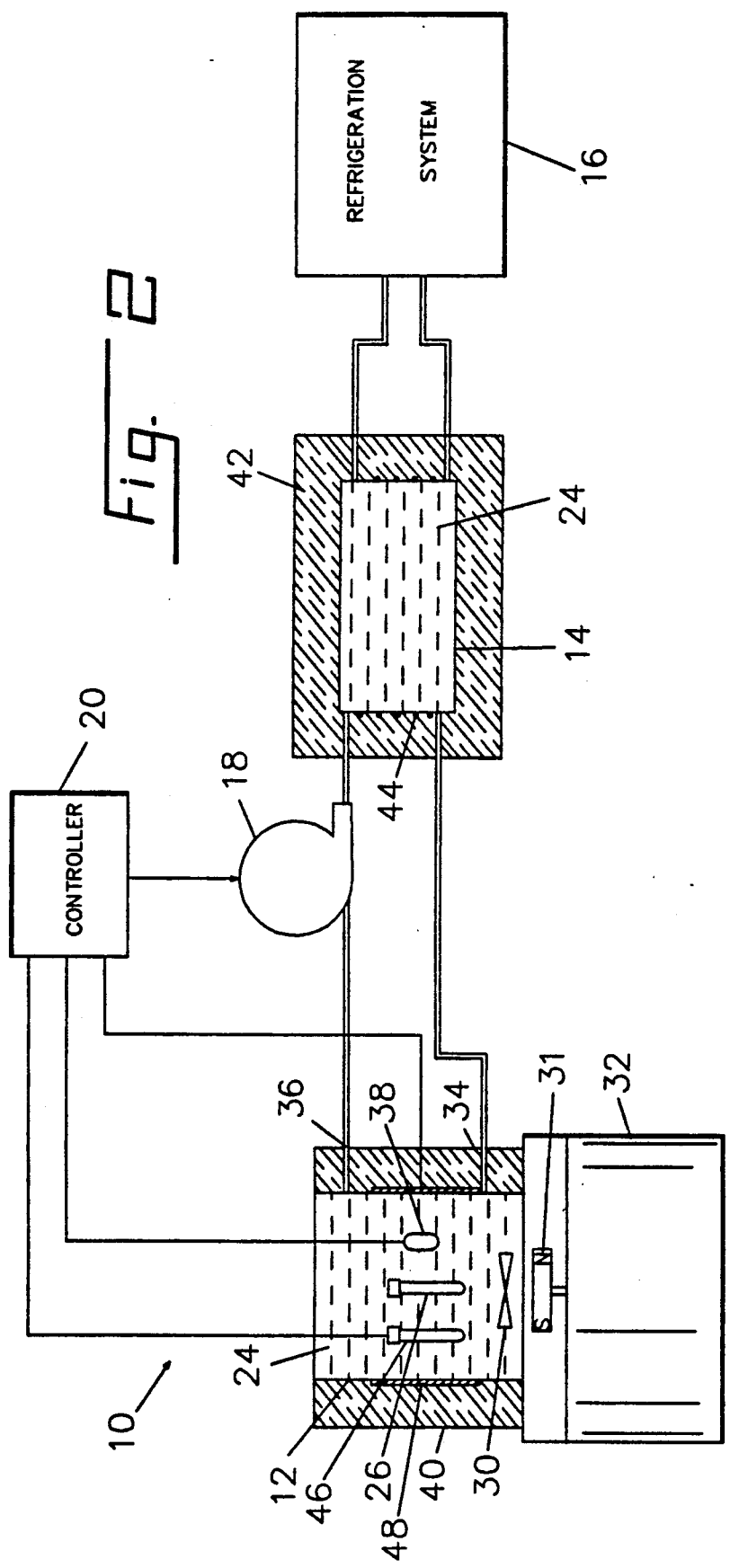

CELL PRESERVATION SYSTEM

BACKGROUND OF THE INVENTION

The present invention relates to techniques for preserving a biological cell specimen.

The preservation of viable cell specimens is a very important field of science. It is essential to long-term preservation of tissue specimens, sperm, and fertilized ovum (zygotes), among others. Cooling of cell specimens to cryogenic temperatures, and then holding the specimens at cryogenic temperatures is typically used for preservation. The cooling must be carefully controlled to minimize crystal size so that crystals are prevented from attaining sizes which are capable of damaging cells. During cooling, the temperature range of from room temperature to about $-40$ to $-50$ degrees Celsius is critical for crystal formation. Precise control of cooling in this range is essential to the viability of the specimen. The most critical temperature range is from about zero degrees C to a few degrees below $-8°$ C. In this range, a specimen releases heat of fusion during cooling. Thus, in this range, the amount of heat which must be removed to maintain a programmed cooling gradient increases markedly. As a consequence, the rate of heat removal requires precise control to maintain a desired cooling rate through this range. Once the speciment is cooled below about $-40°$ or $-50°$ C., crystal formation is no longer a problem, and thus less precise control of the cooling rate is permitted.

The cooling parameters for different lines of cells may differ. Thus, the cooling programs (temperatures, rates and times) for different cell lines may also differ.

At the present, two ways to achieve the cooling of the cells are employed: cooling with a liquified gas (typically liquid nitrogen) and cooling by mechanical refrigeration.

When liquid nitrogen is employed, it is possible to achieve a very high temperature gradient. For example, an initial cooling rate of as much as $80°$ C. per minute is possible. The specimen is usually dipped in a container with liquid nitrogen. Although this gives a large cooling rate, the cooling rate cannot be controlled. Also, liquid nitrogen presents a problem in handling.

Better control of cooling is provided using vapor from a liquified gas (liquid nitrogen). The specimen to be cooled is placed in a vessel with the liquid nitrogen, but out of physical contact with the liquid. The cold vapor coming from the liquid nitrogen is relied on for cooling. This method suffers from the low thermal capacity of a gas. As a consequence, it is difficult to maintain uniform cooling rates and temperatures across a specimen.

Mechanical cooling employs a refrigeration unit that uses coolant coils about the walls of a specimen container. A heat transfer medium, such as, for example, ethanol, in the specimen container aids in the transfer of heat from the specimen to the coolant coils. This technique does not need liquid nitrogen, and can provide cooling down to at least $-80°$ C. However, the temperature gradient attainable by mechanical refrigeration is limited to about 2-3 degrees Celsius per minute. For many biological specimens, this rate is not great enough to prevent the formation of crystals of damaging size through the critical temperature range above $-40°$ C.

OBJECTS AND SUMMARY OF THE INVENTION

It is an object of the invention to provide controlled cooling of a specimen and the ability to achieve high temperature gradients.

It is a further object of the invention to provide a controlled cooling system which does not require the handling of liquified gas.

Briefly stated, a cell preservation system utilizes a pre-chilled coolant, stored in a coolant reservoir, which is pumped at a controlled rate into a vessel containing a specimen. This allows the achievement of a controlled rate of cooling the specimen and controls the formation of crystals in the specimen.

According to an embodiment of the invention, there is provided a system for cooling a specimen comprising: a coolant, a specimen vessel, a coolant reservoir, a coolant in the specimen vessel and the coolant reservoir, means for circulating the coolant between the specimen vessel and the coolant reservoir, means for cooling the coolant in the coolant reservoir, and means for controlling the means for circulating to attain a predetermined rate of cooling of the specimen in the specimen vessel.

According to a feature of the invention, there is provided a process for achieving a controlled cooling of a specimen, comprising: placing a specimen to be cooled in a specimen vessel, prechilling a coolant in a coolant reservoir, circulating the coolant through the coolant reservoir and the specimen vessel at a pumping rate effective for cooling the specimen at a predetermined cooling rate, sizing the coolant reservoir to provide sufficient heat capacity to attain cooling at the predetermined rate.

The above, and other objects, features and advantages of the present invention will become apparent from the following description, read in conjunction with the accompanying drawings, in which like reference numerals designate the same elements.

BRIEF DESCRIPTION OF THE DRAWINGS

FIG. 2 is a schematic drawing of an embodiment of the system of the present invention.

DETAILED DESCRIPTION OF THE PREFERRED EMBODIMENT

Figure 1:
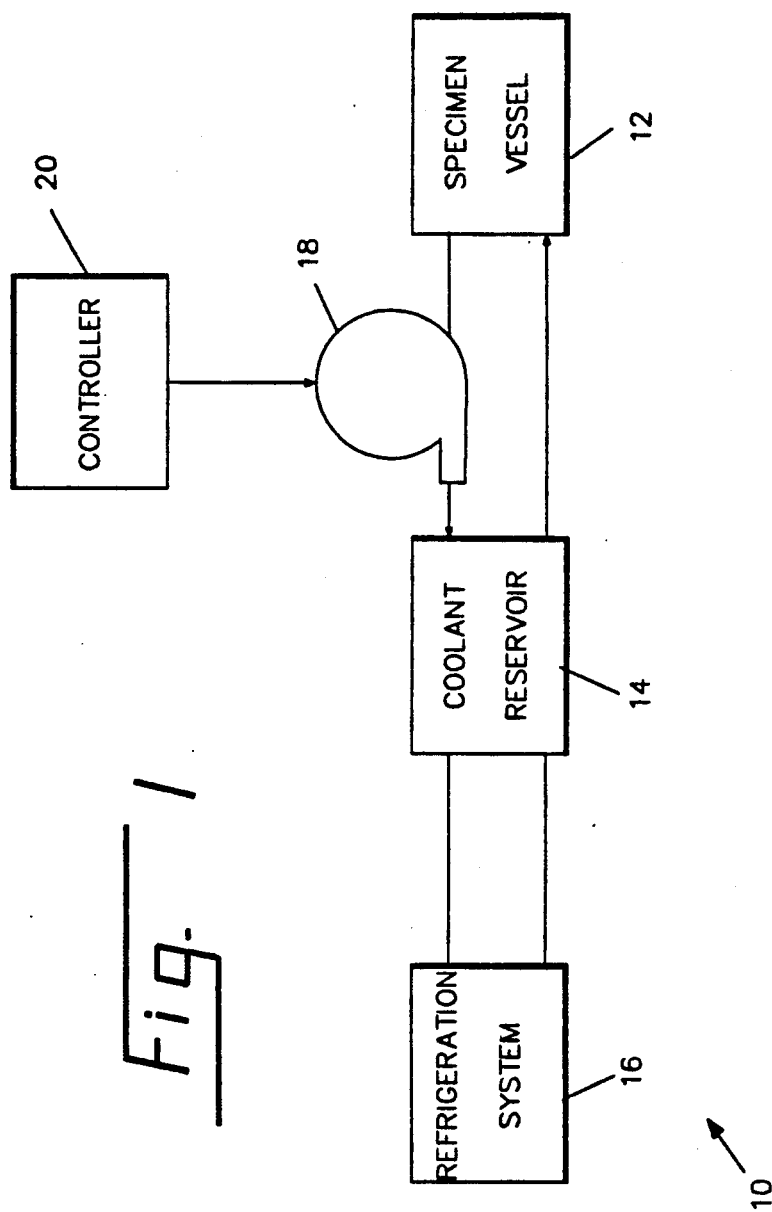
FIG. 1 is a block diagram of the system of the present invention.

Referring to FIG. 1, there is shown, generally at 10, a block diagram of a cell preservation system 10 according to an embodiment of the invention. A specimen vessel 12, for containing a specimen to be cooled, is placed in fluid communication with a coolant reservoir 14 which contains a pre-chilled coolant. The specimen vessel is as seen particularly in FIG. 2, an open top component so coolant present in the specimen vessel is exposed to the ambient environment and hence, coolant present in the specimen vessel is at the same pressure as exists in the ambient environment. The coolant is pre-chilled by refrigeration system 16 communicating with coolant reservoir 14. Coolant reservoir 14 is a sealed reservoir filled with a coolant. The coolant is pumped by pump 18 from a location near the top of specimen vessel 12 into coolant reservoir 14. Since coolant reservoir 14 is sealed, the entry of coolant into the top thereof forces prechilled coolant from the bottom of coolant reservoir 14 to specimen vessel 12. The coolant then exchanges heat with the contents of specimen vessel 12. The initial temperature and heat capacity of the coolant in coolant reservoir 14, and the rate at which pump 18 circulates the coolant, determines the cooling rate of a specimen in specimen vessel 12. That is, if pump 18 is stopped, cooling of a specimen in specimen vessel 12 is limited by the temperature and heat capacity of a heat transfer medium existing in specimen vessel 12. If pump 18 is operated at high speed, substantially the full heat capacity of coolant reservoir 14 is available to cool the specimen. At intermediate speeds of pump 18, intermediate rates of cooling are attained. The pumping speed of pump 18 is controlled by a controller 20.

It is to be noted that pump 18 pumps coolant from a location near the top of specimen vessel 12. Coolant is forced into specimen vessel 12 near its bottom. This has a number of desirable effects. First, any friction heat generated by pump 18 is carried to coolant reservoir 14, rather than to specimen vessel 12. Also, removing coolant from the top of specimen vessel 12, and entering fresh precooled coolant in the bottom of specimen vessel 12, permits stratification of the temperature of the coolant in specimen vessel 12, as will be described hereinafter.

Referring to FIG. 2, cell preservation system 10 includes a coolant 24 in specimen vessel 12. Coolant reservoir 14 is filled with coolant 24 which is pre-cooled by refrigeration system 16. Any suitable coolant can be used in the system of the present invention. The coolant must be of a type that remains fluid at the lowest temperature experienced in the apparatus and must be benign to a specimen placed therein. Examples of suitable coolants include ethanol and silicone oil. A specimen container 26, containing a specimen to be cooled, is placed in specimen vessel 12. Specimen container 26 is surrounded by coolant 24 which provides the cooling. The cooling rate is controlled by changing the speed of pump 18 which, in turn, is controlled by controller 20.

As is conventional, besides a specimen, specimen container 26 may also contain a cryo-protectant fluid. Since the use of a cryo-protectant fluid is conventional, further discussion thereof is unnecessary.

To insure efficient heat exchange between a specimen in specimen container 26 and coolant 24, pre-chilled coolant 24 is delivered to specimen vessel 12 through an inlet pipe 34 located at the bottom of specimen vessel 12. The coolant, heated by contact with specimen container 26, exits specimen vessel 12 through outlet pipe 36 located at the top of specimen vessel 12. To provide a uniform temperature inside the volume of coolant 24, a magnetic stirrer 30 is placed inside specimen vessel 12. Magnetic stirrer 30 is a ferromagnetic mass which may be free inside specimen vessel 12, or may be retained in a bearing for guiding rotation thereof. A permanent magnet 31, outside vessel 12, is rotated by a stirrer motor 32. Magnetic coupling between permanent magnet 31 outside specimen vessel 12, and the ferromagnetic material making up magnetic stirrer 30 inside specimen vessel 12, rotates magnetic stirrer 30 to attain a substantially uniform temperature of coolant 24 therein.

Controller 20 controls the rate at which pre-chilled coolant 24 is delivered into specimen vessel 12. Therefore, if it is desired to increase the rate of cooling in specimen vessel 12, the pumping speed of pump 18 is increased. This allows the achievement of any desired rate of cooling. In addition, the cooling rate can be tailored for different specimens, or can be tailored for different rates at different stages of cooling a particular specimen.

It will be noted that magnetic stirrer 30 maintains a substantially uniform temperature in coolant 24 throughout the interior of specimen vessel 12. At some point in a cooling program, it may be desirable to stop magnetic stirrer 30 to attain maximum cooling of a specimen. This permits temperature stratification to take place in specimen vessel 12. That is, the colder coolant 24, entering near the bottom of specimen vessel 12, is permitted to displace warmer coolant above it so that specimen container 26 is immersed in coolant 24 at substantially the temperature at which it leaves coolant reservoir 14.

Controller 20 may operate open loop. That is, it may operate without feedback informing it of the temperature actually attained in the vicinity of specimen container 26. In one open-loop embodiment, controller 20 contains a microprocessor which controls the pumping rate of pump 18 according to a preset time schedule. The time schedule may be selectable by operator controls according to the type or size of the specimen in specimen container 26. Alternatively, closed-loop control may be achieved using, for example, a conventional temperature probe 38.

Another feedback technique which may be used instead of, or in addition, to temperature probe 38, includes the provision of a dummy specimen container 46 having a temperature probe (not shown) therein. Signals from the temperature probe in dummy specimen container 46 are connected to controller 20. Dummy specimen container 46 preferably contains materials having a temperature and heat capacity closely resembling those of specimen container 26. Thus, the temperature inside dummy specimen container 46 can be expected to follow closely the temperature in specimen container 26.

It is also within the contemplation of the inventor that a temperature probe (not shown) may be inserted into specimen container 26 to measure the temperature therein directly.

Specimen vessel 12 preferably includes a layer of insulation 40 about its exterior to reduce heat loss. Similarly, coolant reservoir 14 includes a layer of insulation 42 about its exterior. Cooling coils 44 are disposed about the exterior of coolant reservoir 14 beneath insulation 42. Alternatively, cooling coils 44 may be disposed inside coolant reservoir 14, either affixed to an inside surface, or suspended within coolant 24.

The size of coolant reservoir 14, the size of specimen vessel 12, the cooling capacity of refrigeration system 16, the amount and rate of heat removal from specimen container 26, and the desired throughput of cell preservation system 10 are interactive parameters. The temperature of coolant 24 in coolant reservoir 14 must remain low enough through the end of a cooling cycle to attain the desired cooling rate. Thus, the initial quantity of coolant 24 in coolant reservoir 14, and its initial temperature must be such that coolant 24 in coolant reservoir 14 has sufficient heat capacity to absorb all of the heat required from a specimen in specimen container 26 to reduce the temperature of the specimen to the desired value, and to do so at the desired cooling rate.

The throughput (number of specimens cooled per hour) is limited by the cooling capacity of refrigeration system 16. In normal operation, refrigeration system 16 operates continuously. During the cooling of a specimen, the temperature of coolant 24 in coolant reservoir 14 rises since refrigeration system 16 is incapable of removing heat as fast as required to attain the desired cooling rate of the specimen. After cooling one or more specimens, the temperature of coolant 24 in coolant reservoir 14 may rise to a value at which effective cooling of a further specimen is not possible. A chilling cycle is then required to decrease the temperature of coolant in coolant reservoir 14 to a value permitting the cooling of further specimens.

In combination, the size of coolant reservoir 14, the size of specimen vessel 12, the control of the pumping of pump 18, the cooling capacity of refrigeration system 16, and the throughput of specimens are interactive parameters. Once these interactive parameters are understood, and cell preservation system 10 is created in accord therewith, controlled cooling of a specimen at any desired rate is possible without incurring the drawbacks of liquid nitrogen coolant.

It will be understood by one skilled in the art that permanent magnet 31 is merely symbolic of a device for producing a rotating magnetic field effective for moving magnetic stirrer 30 inside specimen vessel 12. Other techniques for magnetically driving magnetic stirrer 30 should be considered to fall within the scope of the invention. For example, a plurality of magnetic coils (not shown) may be substituted for permanent magnet 31 and stirrer motor 32. Controller 20 may provide signals for energization of the magnetic coils to provide a moving magnetic field in whose influence magnetic stirrer is forced to move. Preferably, a rotating magnetic field is provided. This should not be taken to exclude a reciprocating magnetic field for some purposes.

Precision of control during cooling may be enhanced by the availability of controlled addition of heat during certain stages. In addition, it may be desirable to raise the temperature of coolant 24 in specimen vessel 12 at the completion of the cooling of one specimen in preparation for the installation of the next specimen. An electric heater 48 is provided optionally on the interior of specimen vessel 12 for these and other purposes. Electric heater 48 may be manually controlled, but is preferably controlled by controller 20.

The presence of electric heater 48 also permits the apparatus to be used for controlled heating of specimens.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

*Pseudo Code*

```
procedure GTACALC

/* Calculate timing data.   */ for each block B do
       DELAY(B) := block delay of B
       for each output O of block B do
          LOAD(O) := fan-out load of O
          end for
       end for for each block B do
       if inputs to B are not yet initialized then
          call INITIALIZE_EXPECTED_TIMES (B)
          end if
       if outputs to B are not yet initialized then
          call INITIALIZE_ACTUAL_TIMES (B)
          end if
       end for subroutine INITIALIZE_EXPECTED_TIMES (B) recursive
       EXPECTED_TIME := 999999;
       for each output O to block B do
          for each fan-out F of output O do
             if expected time of F is not initialized then
                call INITIALIZE_EXPECTED_TIMES (block for F)
                EXPECTED_TIME := min (EXPECTED_TIME, EXPECTED(F))
             end for
          end for
       for each input I to block B do
          EXPECTED(I) := EXPECTED_TIME - DELAY(B)
          end for
       end INITIALIZE_EXPECTED_TIMES subroutine INITIALIZE_ACTUAL_TIMES (B) recursive
       ACTUAL_TIME := -999999;
       for each source S of each input to block B do
```

```
        if actual time of S is not initialized then
            call INITIALIZE_ACTUAL_TIMES (block for S)
        ACTUAL_TIME := max (ACTAUL_TIME, ACTUAL(S))
        end for
    for each output O of block B do
        ACTUAL(O) := EXPECTED_TIME + DELAY(B)
        end for
    end INITIALIZE_EXPECTED_TIMES end GTACALC procedure GTACMPRS /* Compress fan-in trees. */ for each block B do
        if B has exactly one output
            and the output to B has exactly one fan-out
            and ((B is an AND block
                    and the fan-out block is an
                        AND, NAND, AND-OR or AND-NOR block)
                or (B is an OR block
                    and the fan-out block is an
                        OR, NOR, OR-AND or OR-NAND block)
                or (B is an XOR block
                    and the fan-out block is an
                        XOR or NXOR block) then
            transfer the inputs to B to the fan-out block
            delete B
            reassign the rule for fan-out block
            recalculate the changed timing data
            end if
        end for
    end GTACMPRS procedure GTAPREDC /* Delete duplicate parallel blocks. */ for each block B do
        S := source of first input to B
        for each fan-out block F of S do
            if F is equivalent to B then
                transfer the fan-outs of outputs of F to the outputs of B
                delete F
                recalculate the changed timing data
                end if
            end for
        end for
    end GTAPREDC procedure GTAPWRUP (PASSES)

/* Power-up critical blocks. */ repeat PASSES times
        for each block B do
            if SLACK(B) < CRITICAL_SLACK_THRESHOLD then
                BEST_RULE = rule of B
                BEST_DELAY = DELAY(B)
                for each rule R that can be assigned to block B do
                    assign rule R to block B
```

```
        recalculate DELAY(B)
        if DELAY(B) < BEST_DELAY then
          BEST_RULE = R
          BEST_SLACK_B = DELAY(B)
          end if
        end for
      assign rule BEST_RULE to block B
      recalculate the changed timing data
      end if
    end for
  end repeat
end GTAPWRUP
``` procedure GTAREDFO (MARGIN, PASSES)

/* Reduce fan-out load by buffering non-critical fan-outs.  */

```
  repeat PASSES times
    for each block B do
      for each output O of block B do
        if SLACK(O) < CRITICAL_SLACK_THRESHOLD then
          for each fan-out F of output O do
            if F is not the input to a buffer block
                and SLACK(F) >= SLACK(O) + MARGIN then
              buffer F by moving it from O to the output of
                  a buffer block on the fan-out of O
              recalculate the changed timing data
              end if
            end for
          end if
        end for
      end for
    end repeat
  end GTAREDFO
``` procedure GTADUALR

/* Use dual rail blocks to benefit critical paths.  */

```
  for each block B do
    if SLACK(B) < CRITICAL_SLACK_THRESHOLD
        and the technology supports dual rail blocks for B then
      for each output O of block B do
        for each fan-out block F of output O do
          if F is an inverter block then
            if there is no dual rail output of B for O then
              create a dual rail output of B for O then
              reassign the rule for B
              end if
            transfer the fan-out of output of F
                to the dual rail output of B for O
            delete F
            recalculate the changed timing data
            end if
          end for
        end for
      end if
    end for
  end GTADUALR
```

```
procedure GTASINGR

/* Use single rail blocks to benefit critical paths.  */ for each block B do
    if B is dual rail then
      O := most critical output of B
      if SLACK(O) < CRITICAL_SLACK_THRESHOLD
          and B has a dual rail output of O
          and SLACK(dual rail output of O) - DELAY(inverter)
              > SLACK(O) then
        create an inverter block on the fan-out of O
        transfer the fan-out of the dual rail output of O
            to the output of the inverter block
        delete the dual rail output of O
        reassign the rule for B
        recalculate the changed timing data
      end if
    end for
end GTASINGR procedure GTASINVT /* Swap inverterd with non-inverted fan-outs.  */ for each block B do
    if SLACK(B) < CRITICAL_SLACK_THRESHOLD
        and B is invertable
        and there is a fan-out block F of B that is an inverter
        and SLACK(F) = SLACK(B) then
      invert the function of B
      swap the fan-out of B except that of the inverter
          with the fan-out of the inverter
      reassign the rule for B
      recalculate the changed timing data
      end if
    end for
end GTASINVT procedure GTAMINVT (PASSES)

/* Create parallel inverted blocks.  */ repeat PASSES times
    for each block B do
      if SLACK(B) < CRITICAL_SLACK_THRESHOLD
          and B is invertable
          and there is a fan-out block F of B that is an inverter
          and SLACK(F) = SLACK(B) then
          and there is a fan-out block of F' that is not an inverter
          and SLACK(F') - DELAY(inverter) < SLACK(B) then
        create a copy of block B but with inverted function
        transfer the fan-out of the inverter
            to the inverted copy of B
        deleted the inverter fan-out block
        assign a rule for the inverted copy of B
        recalculate the changed timing data
        end if
      end for
    end repeat PASSES times
end GTAMINVT
```

```
procedure GTADEMOR (MARGIN, PASSES)

/* Apply DeMorgan's Rule where beneficial.  */ repeat PASSES times
    for each block B do
      if B is a AND, OR, NAND, or NOR block
        and ((SLACK(B) < CRITICAL_SLACK_THRESHOLD
              and SLACK(every input source of B into which
                         an inverter would have to be inserted)
                 > SLACK(B) + MARGIN)
          or (SLACK(B) >= CRITICAL_SLACK_THRESHOLD
              and applying DeMorgan'S Rule would reduce
                  the number of inverter blocks)) then
        invert the inputs signals coming into B
        change the function of B to NOR, NAND, OR, AND respectively
        reassign the rule for B
        recalculate the changed timing data
        end if
      end for
    end repeat
  end GTADEMOR procedure GTACAND (MARGIN, PASSES)

/* Compress critical AND blocks into critical fan-out blocks.  */

/* GTACAO is similar, but works with AND-OR blocks instead.  */ repeat PASSES times
    for each block B do
      if SLACK(B) < CRITICAL_SLACK_THRESHOLD
         and B is an AND block then
        for each fan-out block F of the output of block B do
          if F is an AND, OR, NAND, NOR, AND-OR, or AND-NOR block
             and SLACK(input of F whose source is B) = SLACK(B)
             and SLACK(every other input of F) >= SLACK(B) + MARGIN
             then
            copy the inputs of B to F
            remove F from the fan-out of the output of B
            if the output of B has no fan-outs then delete B
            reassign the rule for F
            recalculate the changed timing data
          end for
        end if
      end for
    end repeat
  end GTACAND procedure GTABAO (MAX_CRITICAL_GROUPS, MARGIN)

/* Break-off non-critical groups from critical compound blocks.  */ for each block B do
    if SLACK(B) < CRITICAL_SLACK_THRESHOLD
       and B is an AND-OR, AND-NOR, OR-AND, or OR-NAND block
       and B has at least two groups such that
           SLACK(group) >= SLACK(B) + MARGIN
       and B has no more than MAX_CRITICAL_GROUPS groups such that
           SLACK(group) < SLACK(B) + MARGIN then
      create an AND-OR, AND-OR, OR-AND, or OR-AND block
          for B respectively
      transfer the "non-critical" groups of B to the new block
      link the new block to B
```

```
      if each group of B now only has one input then
        change the function of B to OR, NOR, AND, NAND respectively
        end if
      reassign the rule for B
      assign the rule for the new block
      recalculate the changed timing data
      end if
    end for
  end GTABAO procedure GTAREGRP /* Regroup critical compound blocks so that the most critical
     path through the block takes the fastest path through the
     block.  */ for each block B do
    if SLACK(B) < CRITICAL_SLACK_THRESHOLD
        and B is a AND-OR, AND-NOR, OR-AND, or OR-NAND block then
      repeat number of groups of B -1 times
        OLD_G := most critical group of B
                 that has not been reassigned
        NEW_G := group with fastest path through B
                 that has not had a group reassigned to it
        swap inputs of group OLD_G with inputs of group NEW_G
        mark OLD_G as an assigned critical group
        end repeat
      recalculate the changed timing data
      end if
    end for
  end GTAREGRP procedure GTAREDFI (MAX_CRITICAL_INPUTS,
                    MIN_NON_CRITICAL_INPUTS,
                    MARGIN)

/* Break-off non-critical inputs from critical blocks.  */ for each block B do
    if SLACK(B) < CRITICAL_SLACK_THRESHOLD
        and B is an AND, OR, XOR, NAND, NOR, NXOR,
                    AND-OR, AND-NOR, OR-AND, or OR-NAND block then
      for each input group G of B do
        if G has at least MIN_NON_CRITICAL_INPUTS inputs such that
             SLACK(input) >= SLACK(G) + MARGIN
           and G has no more than MAX_CRITICAL_INPUTS inputs such that
             SLACK(input) < SLACK(G) + MARGIN then
          create an AND, OR, XOR, AND, OR, XOR,
                    AND, AND, OR, or OR block for G respectively
          transfer the "non-critical" inputs of G to the new block
          link the new block to group G of B
          if B is a AND-OR, AND-NOR, OR-AND, or OR-NAND block
              and each group of B now only has one input then
            change the function of B to OR, NOR, AND, NAND respectively
            end if
          reassign the rule for B
          assign the rule for the new block
          recalculate the changed timing data
          end if
        end for
      end if
    end for
  end GTAREDFI
```

```
procedure GTAFI

/* Correct blocks with fan-in violations.  */ for each block B do
    if B is an AND, OR, XOR, NAND, NOR, NXOR
              AND-OR, AND-NOR, OR-AND, or OR-NAND block then
      for each input group G of B do
        if the number of inputs of B in this group >
           the number of inputs for this group supported
           by the rule assigned to B then
          create a tree of AND, OR, XOR, AND, OR, XOR,
                           AND, AND, OR, OR blocks for group G
                           of block B respectively with group G
                           of block B as the root
          transfer the least critical of the excess inputs of group G
               to leaves of the tree
          assign each non-root node of the tree a rule
          recalculate the changed timing data
        end for
      end if
    end for
  end GTAFI procedure GTAFIXOR (MIN_FAN_IN, MAX_FAN_IN)

/* Break-up big critical XOR blocks.  */ for each block B do
    if SLACK(B) < CRITICAL_SLACK_THRESHOLD
       and B is an XOR block
       and B has at least MIN_FAN_IN inputs then
      break-up B into a tree of XOR blocks, each of which has
           no more than MAX_FAN_IN inputs
      assign each node of the tree a rule
      recalculate the changed timing data
    end if
  end for
  end GTAFIXOR procedure GTAUNBUF (PASSES)

/* Remove buffer blocks from critical paths. */ repeat PASSES times
    for each block B do
      if SLACK(B) < CRITICAL_SLACK_THRESHOLD
         and B is a buffer block
         and SLACK(source block of input to B) = SLACK(B) then
        F := fan-out of output of B with SLACK(F) = SLACK(B)
        transfer F from the fan-out of the output of B
             to the fan-out of the source of the input to B
        if the output of B has no fan-outs then
          delete B
        end if
        recalculate the changed timing data
      end if
    end for
  end repeat
  end GTAUNBUF
```

```
procedure GTAFO (MARGIN)

/* Correct blocks with output pins with fan-in load violations.  */ for each block B do
    for each output O of block B do
      if the LOAD(O) > that allowed by the rule assigned to B then
          and SLACK(B) < CRITICAL_SLACK_THRESHOLD + MARGIN
        if SLACK(B) < CRITICAL_SLACK_THRESHOLD
            and B is a small block then
          create enough copies of block B to which sufficient
              fan-out of O can be transferred so that LOAD(O)
              is reduced to acceptable levels
        else
          create buffer blocks that fan-out from O to which sufficient
              fan-out of O can be transferred so that LOAD(O)
              is reduced to acceptable levels
        end if
        recalculate the changed timing data
      end if
    end for
  end for
end GTAFO procedure GTAFOBAL /* Balance the fan-out load among equivalent outputs so as to
     maximize their slacks.  */ for each set S of equivalent outputs do
    TOP_OF_LOOP:

O := most critical output in S
    if O is critical then
      OLD_SLACK_O := SLACK(O)
      F := most critical fan-out of O
      for each output O' of set S do
        if O' ¬= O then
          transfer F from the fan-out of O
              to the fan-out of O'
          recalculate the changed timing data
          if SLACK(O') > OLD_SLACK_O then
            goto TOP_OF_LOOP
          end if
          transfer F from the fan-out of O'
              back to the fan-out of O
          recalculate the changed timing data
        end if
      end for for each output O' of set S do
        if O' ¬= O then
          for each fan-out F' of output O' do
            transfer F from the fan-out of O
                to the fan-out of O'
            transfer F' from the fan-out of O'
                to the fan-out of O
            recalculate the changed timing data
            if SLACK(O') > OLD_SLACK_O
                and SLACK(O) > OLD_SLACK_O then
              goto TOP_OF_LOOP
            end if
            transfer F from the fan-out of O'
                back to the fan-out of O
            transfer F' from the fan-out of O
                back to the fan-out of O'
```

```
            recalculate the changed timing data
          end for
        end if
      end for
    end if
  end for
end GTAFOBAL procedure GTAPROMO (MARGIN, XOR_MARGIN, PASSES)

/* Promote critical inputs to fan-out blocks.  */ repeat PASSES times
    for each block B do
      if SLACK(B) < CRITICAL_SLACK_THRESHOLD
          and B is an AND, OR, or XOR block then
        for every fan-out block F of the output of B do
          if ((B is an AND block)
                and (F is not an AND, NAND, AND-OR, or AND-NOR block))
              or ((B is an OR block)
                and (F is not an OR, NOR, OR-AND, or OR-NAND block))
              or ((B is an XOR block)
                and (F is not an XOR or NXOR block)) then
            goto NEXT_BLOCK
          end if
          if there is no rule that supports another input to F then
            goto NEXT_BLOCK
          end if
          for each input I of block F do
            if the source of I is not B
                and ((B is an AND or OR block
                      and SLACK(I) - MARGIN < SLACK(B))
                  or (B is an XOR block
                      and SLACK(I) - XOR_MARGIN < SLACK(B)) then
              goto NEXT_BLOCK
            end if
          end for
        end for I := most critical input to B
        for every fan-out block F of the output of B do
          copy input I from to fan-out block F
          reassign the rule for fan-out block F
        end for
        delete input I from block B
        if block B has only one input then
          remove B from the logic
        else
          reassign the rule for block B
        end if
        recalculate the changed timing data
      end if NEXT_BLOCK:
    end for
  end repeat
end GTAPROMO procedure GTASIN (PASSES)

/* Swap critical with non-critical inputs.  */ repeat PASSES times
    for each block B do
```

```
      if SLACK(B) < CRITICAL_SLACK_THRESHOLD
         and B is an AND, OR, or XOR block
         and B has exactly one output O
         and O has exactly one fan-out block F
         and SLACK(F) = SLACK(B) then
        OLD_SLACK_F = SLACK(F)
        I := most critical input to B
        I' := most critical input to F
        if the source block of I' ¬= B then
           transfer input I from block B to block F
           transfer input I' from block F to block B
           recalculate the changed timing data
           if SLACK(F) < OLD_SLACK_F then
              transfer input I from block B back to block B
              transfer input I' from block F back to block F
              recalculate the changed timing data
           end if
        end if
     end for
  end repeat
end GTASIN procedure GTACELDN /* Choose rules for non-critical blocks that minimizes size.   */ for each block B do
     if SLACK(B) >= CRITICAL_SLACK_THRESHOLD then
        BEST_RULE = rule of B
        BEST_SIZE_B = size of rule of B
        for each rule R that can be assigned to block B do
           if size of R < BEST_SIZE_B then
              assign rule R to block B
              recalculate the changed timing data
              if SLACK(B) > CRITICAL_SLACK_THRESHOLD then
                 BEST_RULE = R
                 BEST_SIZE_B = size of rule R
              end if
           end if
        end for
        assign rule BEST_RULE to block B
        recalculate the changed timing data
     end if
  end for
end GTACELDN procedure GTAREPWR (MIN_IMPROVEMENT)

/* Choose rules for critical blocks that maximizes slack.   */ for each block B do
     if SLACK(B) < CRITICAL_SLACK_THRESHOLD then
        BEST_RULE = rule of B
        BEST_SLACK_B = SLACK(B)
        for each rule R that can be assigned to block B do
           assign rule R to block B
           recalculate the changed timing data
           if SLACK(B) > BEST_SLACK_B then
              BEST_RULE = R
              BEST_SLACK_B = SLACK(B)
           end if
        end for
        assign rule BEST_RULE to block B
        recalculate the changed timing data
     end if
  end for
end GTAREPWR
```

What is claimed:

1. A system for cooling a specimen comprising:
a specimen vessel in which the specimen to be cooled is received;
a sealed coolant reservoir;
a coolant in said specimen vessel and said coolant filling said reservoir, said specimen vessel having an open top whereby the coolant therein is exposed to ambient environment;
means for circulating a flow of said coolant between said specimen vessel and said coolant reservoir whereby an inflow of coolant from said specimen vessel to said coolant reservoir at a first reservoir location causes an outflow of coolant from a second reservoir location as a return flow to said specimen vessel;
means for cooling said coolant in said coolant reservoir; and
means for controlling said means for circulating to attain a predetermined rate of cooling of said specimen in said specimen vessel.

2. A system according to claim 1, further comprising means for agitating said coolant in said specimen vessel, whereby a substantially uniform temperature is maintained therethrough.

3. The system of claim 2, wherein said means for agitating includes:
a magnetic stirrer in said specimen vessel;
means for producing a moving magnetic field in said specimen vessel; and
said magnetic stirrer and said moving magnetic field being magnetically coupled, whereby said magnetic stirrer is moved inside said specimen vessel to stir said coolant therein.

4. A system according to claim 1, wherein said means for circulating includes:
a pump;
said pump being connected to pump said coolant from said specimen vessel to said coolant reservoir, pressure developed in said coolant reservoir from pumping said coolant thereunto forcing said coolant from said reservoir to said specimen vessel.

5. A system according to claim 1, further comprising a controller controlling at least said means for circulating to produce circulation at a rate effective for attaining said predetermined rate of cooling.

6. A system according to claim 5, wherein said rate includes zero.

7. A system according to claim 1, further comprising a heater in said specimen vessel.

8. A system for cooling a specimen comprising:
a specimen vessel;
a coolant reservoir;
a coolant in said specimen vessel and said coolant reservoir;
means for circulating said coolant between said specimen vessel and said coolant reservoir;
means for cooling said coolant in said coolant reservoir; and
means for controlling said means for circulating to attain a predetermined rate of cooling of said specimen in said specimen vessel, said controlling means including
a pump;
said pump being connected for circulating said coolant between said coolant reservoir and said specimen vessel;
a controller;
means for sensing a temperature in said specimen vessel; and
said controller controlling a pumping speed of said pump in response to said temperature.

9. A system for controlled cooling of a specimen, comprising:
a specimen vessel in which a specimen to be cooled is received;
a sealed coolant reservoir;
a coolant in said specimen vessel and said coolant filling said reservoir, said specimen vessel having an open top whereby the coolant therein is exposed to ambient environment;
a refrigeration system;
means for permitting said refrigeration system to precool said coolant in said coolant reservoir;
a coolant pump;
said coolant pump being effective to circulate a flow of coolant between said specimen vessel and said reservoir whereby an inflow of coolant from said specimen vessel to said coolant reservoir at a first reservoir location causes an outflow of coolant from a second reservoir location as a return flow to said specimen vessel; and
means for controlling said coolant pump to control a temperature in said specimen vessel.

10. A system according to claim 9, wherein said coolant enters said specimen vessel near a bottom end thereof.

11. A system according to claim 9, wherein said coolant pump is effective to pump said coolant from an upper portion of said coolant reservoir.

* * * * *

UNITED STATES PATENT AND TRADEMARK OFFICE
CERTIFICATE OF CORRECTION

PATENT NO. : 5,003,787

DATED : April 2, 1991

INVENTOR(S) : Yury Zlobinsky

It is certified that error appears in the above-identified patent and that said Letters Patent is hereby corrected as shown below:

Column 6, line 28 to the end of column 24, should be deleted.

Signed and Sealed this

Twenty-fifth Day of August, 1992

Attest:

DOUGLAS B. COMER

Attesting Officer

Acting Commissioner of Patents and Trademarks